United States Patent
Carr

(10) Patent No.: US 10,869,605 B2
(45) Date of Patent: Dec. 22, 2020

(54) NONINVASIVE MICROWAVE RADIOMETRIC SENSING OF A TYMPANIC MEMBRANE

(71) Applicant: Applied Thermologic, LLC, Woolwich, ME (US)

(72) Inventor: Kenneth L. Carr, Woolwich, ME (US)

(73) Assignee: Applied Thermologic, LLC, Woolwich, ME (US)

( * ) Notice: Subject to any disclaimer, the term of this patent is extended or adjusted under 35 U.S.C. 154(b) by 0 days.

(21) Appl. No.: 16/211,573

(22) Filed: Dec. 6, 2018

(65) Prior Publication Data

US 2019/0175025 A1 Jun. 13, 2019

Related U.S. Application Data

(60) Provisional application No. 62/596,623, filed on Dec. 8, 2017.

(51) Int. Cl.
*A61B 5/01* (2006.01)
*A61B 5/00* (2006.01)
(Continued)

(52) U.S. Cl.
CPC ............ *A61B 5/015* (2013.01); *A61B 5/0008* (2013.01); *A61B 5/02055* (2013.01);
(Continued)

(58) Field of Classification Search
CPC combination set(s) only.
See application file for complete search history.

(56) References Cited

U.S. PATENT DOCUMENTS

| 5,496,271 A * | 3/1996 | Burton | A61B 18/18 604/101.05 |
| 2007/0299488 A1* | 12/2007 | Carr | A61B 5/01 607/101 |

(Continued)

OTHER PUBLICATIONS

Ludeke et al. (1983) "Microwave radiometric system for biomedical 'true temperature' and emissivity measurements." J Microwave Power, 18, 8 pp.

(Continued)

*Primary Examiner* — Lee S Cohen
*Assistant Examiner* — Tigist S Demie
(74) *Attorney, Agent, or Firm* — Lathrop GPM LLP

(57) ABSTRACT

A microwave radiometric sensor probe module configured to fit within at least an external portion of an auditory or ear canal of a patient encloses a microwave integrated circuit and associated waveguide printed probe. The probe is configured to receive microwave radiation from a dielectric rod antenna of the module oriented into the auditory canal towards a tympanic membrane. Radiation from the tympanic membrane is coupled into the rod antenna, projected towards the printed probe, and received at the integrated circuit. A communications interface connects the integrated circuit to a temperature monitor and control unit for receiving the sensor output and for deriving at least a measure of patient brain temperature from the sensor output. The temperature monitor and control unit may be connected to a targeted temperature management system for controlling the temperature of a patient on the basis of the derived brain temperature.

24 Claims, 5 Drawing Sheets

(51) Int. Cl.
    *A61B 5/0205*     (2006.01)
    *A61F 7/12*     (2006.01)
    *A61F 7/00*     (2006.01)
    *G01K 5/00*     (2006.01)
    A61B 5/024     (2006.01)
    A61B 5/08     (2006.01)
    A61F 7/02     (2006.01)

(52) U.S. Cl.
    CPC .......... *A61B 5/4064* (2013.01); *A61B 5/4836* (2013.01); *A61B 5/6817* (2013.01); *A61B 5/7278* (2013.01); *A61B 5/742* (2013.01); *A61F 7/00* (2013.01); *A61F 7/123* (2013.01); *G01K 5/00* (2013.01); A61B 5/024 (2013.01); A61B 5/0507 (2013.01); A61B 5/0816 (2013.01); A61B 2560/0412 (2013.01); A61B 2562/0228 (2013.01); A61B 2562/164 (2013.01); A61B 2562/182 (2013.01); *A61F 2007/0002* (2013.01); *A61F 2007/0006* (2013.01); *A61F 2007/0007* (2013.01); *A61F 2007/0056* (2013.01); *A61F 2007/0095* (2013.01); *A61F 2007/0233* (2013.01)

(56) References Cited

U.S. PATENT DOCUMENTS

2015/0119870 A1*   4/2015   Rudie ................ A61B 18/1815
    606/33
2018/0274990 A1*   9/2018   Park ........................ A61B 5/01

OTHER PUBLICATIONS

Carr et al. (1983) "The effect of antenna match on microwave radiometric thermal patterns." IEEE MTT DIG F-5, 189, 3 pp.

* cited by examiner

NONINVASIVE MICROWAVE RADIOMETRIC SENSING OF A TYMPANIC MEMBRANE

CROSS REFERENCE TO RELATED APPLICATIONS

This application claims priority to U.S. Provisional Application No. 62/596,623 filed on Dec. 8, 2017, the contents of which is hereby incorporated by reference in its entirety.

STATEMENT REGARDING FEDERALLY SPONSORED RESEARCH OR DEVELOPMENT (Not Applicable)

BACKGROUND

Various embodiments relate generally to systems and methods for the accurate measurement of brain temperature in mammals, and humans in particular. This section is intended to provide a background or context. The description may include concepts that may be pursued, but have not necessarily been previously conceived or pursued. Unless indicated otherwise, what is described in this section is not deemed prior art to the description and claims and is not admitted to be prior art by inclusion in this section.

Hypoxic-ischemia or asphyxia is a serious problem in newborns. Lack of an adequate supply of oxygenated blood to the brain, or intrapartum asphyxia, may result in a serious brain injury called hypoxic-ischemic encephalopathy (HIE). The newborn's body can compensate for brief periods of depleted oxygen, but if the asphyxia lasts too long, brain tissue is destroyed. It is estimated that HIE occurs in about 3-5 newborns out of 1,000 term infants. About half of these infants with HIE (range of 35-50%) will die or suffer from severe handicaps such as mental retardation or cerebral palsy. HIE due to fetal or neonatal asphyxia is a leading cause of death or severe impairment among infants.

High-quality, randomized, controlled trials have proven that induced hypothermia, or hypothermia therapy (HT), in post-asphyxia encephalopathy is safe. In addition, it has been proven to significantly reduce the incidence of death and disability. The aim is to cool infants with moderate or severe HIE within six hours of birth to a body temperature between 32.5° C. and 33.5° C. and maintain this degree of cooling without interruption for 72 hours, followed by a slow rewarming over at least twenty hours at a rate of 0.2° C. per hour until their temperature reaches a desired range of 36.5-37° C.

Currently, trials effecting hypothermic cooling of the head or systemic hypothermia utilize rectal temperature as an indirect index of the infant's brain temperature. However, while performing hypothermic cooling, it is necessary not only to control brain temperature but also to control the rate of cooling, as well as the rate of re-warming the brain. Such close control cannot be maintained by measuring temperature at a remote site such as the rectum. Importantly, newborns with HIE may have a brain temperature that is elevated with respect to rectal temperature by as much as 3° C.

Targeted temperature management (TTM) is an active treatment for reducing the risk of brain tissue injury following lack of blood flow. Such periods of poor blood flow may be related to cardiac arrest, blockage of an artery such as by a blood clot as in the case of a stroke, or traumatic brain injury (TBI). By lowering body temperature to a target level and maintaining the temperature level for a given period of time, brain function following resuscitation from cardiac arrest may be improved. In adults, current techniques require the measurement of core body temperature via the esophagus, rectum, bladder, or within the pulmonary artery to guide cooling. However, as it is brain tissue damage that is being mitigated by TTM, precise monitoring of the brain would appear to be required to provide optimal results.

It is also possible to measure deep brain temperature non-invasively using magnetic resonance spectroscopy, but the cost and feasibility are significant detractions with this approach considering the need for continuous 72-hour thermal monitoring of each newborn in a ferromagnetic-free environment, followed by a 16-24 hour re-warming period, bringing the total time for each hypothermia procedure to about 94 hours.

The monitoring of axillary esophageal and nasopharyngeal temperatures to indicate intracranial temperature has also been considered. However, these areas, like the rectal area, are slow in indicating thermal trends in the brain.

It has been proposed to non-invasively detect and monitor intracranial temperature of a newborn undergoing hypothermic treatment both at depth and at a surface using microwave radiometry (i.e. surface of the head rather than at the tympanic membrane). However, such a system as tested generated unreliable temperature measurements and proved unable to provide the temperature detection accuracy required to safely implement hypothermic treatment in infants.

In adults, the measurement of temperature in the jugular bulb is considered equivalent to the measurement of brain temperature but it is an invasive procedure with associated risk. The jugular bulb is a venous structure located close to the tympanic membrane and the inner ear and is the dilated part of the interior jugular vein. The jugular bulb, however, is not present at birth and only develops over time. The tympanic membrane, which is in close proximity to the jugular vein, is highly vascular and, as with the jugular bulb, receives blood from the brain.

Measuring temperature at the tympanic membrane, therefore, is considered a more reliable indicator of true core temperature as compared to prior art and conventional techniques such as rectal temperature.

There are available devices based on infrared (IR) technology which may be placed in the ear. However, these so-called tympanic devices, although relatively inexpensive, are still not considered sufficiently accurate for this application. IR temperature detection is an example of clinical radiometry, or the measurement of natural emission from the body. The intensity of emission increases with increasing temperature. The intensity of emission is also dependent on the absorption characteristics of the tissue involved; the higher the loss tangent or absorption, the higher the emissivity. Ear wax and moisture in the ear are very absorptive at IR frequencies. Also, such devices actually measure radiation from the ear canal wall and the environment within the ear canal, thus resulting in a lower temperature reading than would be obtained from the tympanic membrane itself. Still further, the available IR devices are physically large and therefore not suited for insertion into the ear of a newborn patient who, as noted above, may require continuous monitoring for many hours. Finally, commercially available IR devices do not read below 34° C., while the preferred temperature range for intracranial cooling is 32.8-33.0° C.

In sum, the prior apparatus are disadvantaged in that they do not measure the brain parenchymal tissue directly but rather rely on indirect temperature measurements on other parts of the body.

Accordingly, it would be desirable to provide apparatus and methods for reliably detecting and monitoring brain temperature at depth during long-term hypothermic treatment to reduce the incidence of brain injury particularly in newborns.

BRIEF SUMMARY

In a first aspect, the present invention pertains to a system for and method of using noninvasive microwave radiometric sensing to measure and monitor the temperature of the tympanic membrane, from which the temperature of the brain may be inferred.

In another aspect, the present invention provides a device for noninvasive microwave radiometric sensing including a microwave housing comprised of a microwave integrated circuit, a printed probe, a dielectric filled waveguide, and an antenna, preferably a dielectric rod antenna.

In a further aspect, the present invention pertains to a sensor probe system for and method of non-invasively measuring and monitoring over time the temperature of a tympanic membrane of a patient as derived from the microwave emissions detected by passive microwave radiometry.

In another aspect, the present invention pertains to a method of detecting patient respiration rate and heart rate via passive microwave radiometry with respect to a tympanic membrane of the patient.

In another aspect, the present invention pertains to a sensor probe module for passive microwave radiometry configured to fit at least within the external auditory canal of a patient, the tissue of the auditory canal acting as a filter and absorber to external microwave interference.

In another aspect, the present invention pertains to a sensor probe module for passive microwave radiometry configured to fit at least within the external auditory canal of a patient and having a passive depth sensing and reporting apparatus for detecting proximity of a portion of the module to a tympanic membrane of a patient. To insure accuracy, the distance between the distal end of the probe and the tympanic membrane must be controlled to avoid the probe making contact with the membrane. This distance can be derived by the measurement of reflection coefficient determined by the use of a reflectometer such as a noise injection radiometer. The injection of low level noise from the radiometer can be used to determine the match or percentage of the signal reflected.

In another aspect, the present invention pertains to a system for and method of detecting and monitoring the tympanic membrane temperature of a patient through non-invasive radiometric measurement for deriving the brain temperature of the patient from the detected tympanic membrane temperature, and for controlling a targeted temperature management (TTM) system based upon the derived brain temperature measurement.

The presently disclosed microwave radiometric sensor probe module comprises in a first embodiment a housing configured to fit within at least an external portion of an auditory or ear canal of a patient. The housing encloses a microwave integrated circuit and associated waveguide printed probe. The probe is configured to receive microwave radiation from a dielectric rod antenna oriented into the auditory canal towards the tympanic membrane. In one embodiment, the housing is provided with cabling for biasing the microwave integrated circuit and for receiving the output of the circuit indicative of the received microwave signal from the tympanic membrane. The cabling is connected to a temperature monitor and control unit for providing the bias voltage, for receiving the sensor output, and for deriving measures of patient brain temperature, respiratory rate, and heart rate from the sensor output. A user interface associated with the temperature monitor and control unit may provide an indication of the derived measure of brain temperature from the observed tympanic membrane temperature and may enable a user to define desired or acceptable values of brain temperature, respiratory rate, or heart rate to a user.

In an alternative embodiment, the microwave radiometric sensor probe module is provided with a power supply such as in the form of a small battery located within the probe itself or on or adjacent the patient and connected to the probe via a short, flexible cable. In further embodiments, the module further comprises a wireless interface with sufficient transmission power to communicate with a local temperature monitor and control unit, as described above. This embodiment provides the benefit of reducing the number of wires present, particularly with respect to an HIE patient.

In a further embodiment, the temperature monitor and control unit is connected to a TTM system for controlling the temperature of a patient on the basis of the measured tympanic membrane temperature, from which a measure of brain temperature may be derived.

The housing may be provided having an external portion shaped in the form of a traditional ear specula for an otoscope.

Methods of using the system for deriving a measure of the brain temperature, respiratory rate, and/or heart rate of a patient using a microwave radiometric sensor probe module are also disclosed. Such methods include detecting energy radiated by a tympanic membrane of a patient using a dielectric antenna coupled to a passive microwave probe. A microwave integrated circuit coupled to the passive microwave probe conveys the detected energy to a temperature monitor and control unit, which derives the measure of brain temperature, respiratory rate, and/or heart rate therefrom.

In another method, the measure of brain temperature, derived from the observed tympanic membrane temperature, is compared to a preset temperature value within the temperature monitor and control unit and, in response to the comparison, a TTM system is controlled by the temperature monitor and control unit in order to adjust the brain temperature of the patient. The functions of the temperature monitor and control unit and the TTM system may be implemented by discrete intercommunicating systems in one embodiment or may be implemented within a single device.

BRIEF DESCRIPTION OF THE SEVERAL VIEWS OF THE DRAWINGS

Aspects of the described embodiments are more evident in the following description, when read in conjunction with the attached Figures.

DETAILED DESCRIPTION

Various embodiments allow a user to derive a measure of the brain temperature of a patient through radiometric sensing of energy emitted from a tympanic membrane of the patient. A microwave radiometric sensor probe module 10 is inserted at least partially within an ear canal of a patient. The module is compact and lightweight, thereby enabling its continuous use for extended periods of time, such as through the duration of a targeted temperature management (TTM) treatment regimen. Tympanic radiation detection enables a highly accurate determination of the brain temperature of a patient in real time. Because of the close proximity between the tympanic membrane and jugular vein and because blood exiting the brain flows through the jugular vein, the temperature of the tympanic membrane is regarded as indicative of the temperature of the brain. In other words, brain temperature may be derived or determined from the measured tympanic membrane temperature.

Radiometry is the passive measurement of received radiation. Radiometry is defined as the technique for measuring electromagnetic energy considered as thermal radiation. Clinical Radiometry, in turn, is the measurement of natural emission from the human body. Any object above absolute zero will radiate electromagnetic energy to an extent governed by its radiant emittance. Tympanic radiation detection, as disclosed herein, is thus distinguished from ionizing radiation detection.

Figure 2:
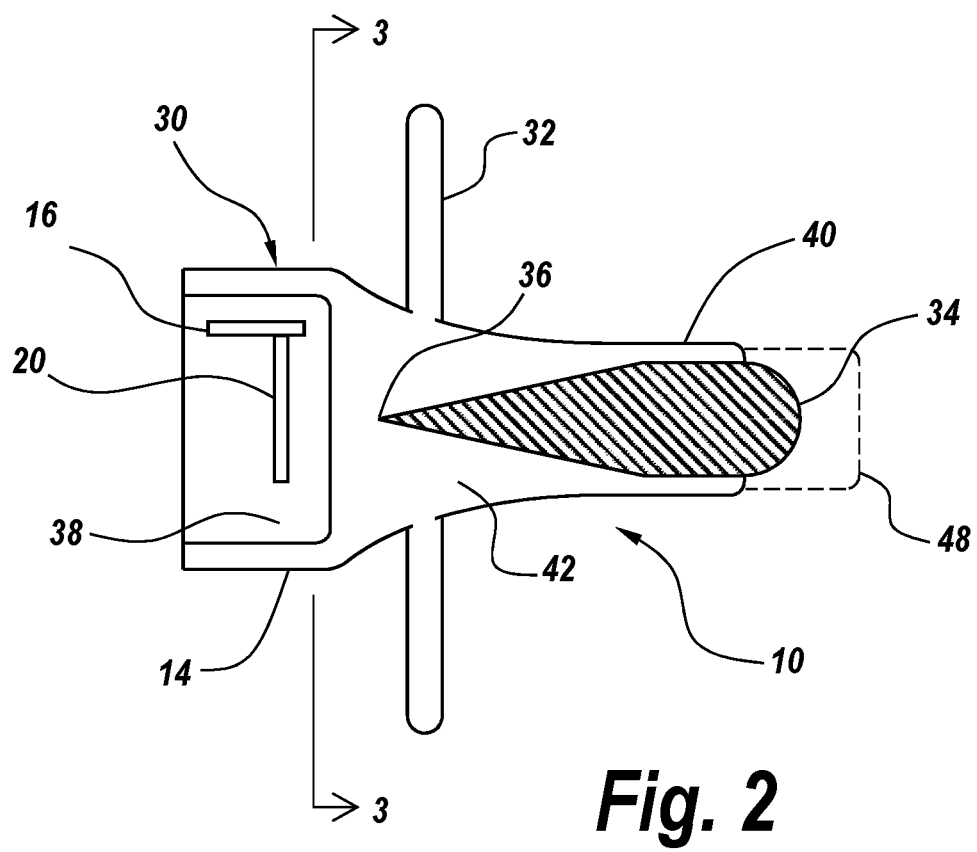
FIG. 2 is a side section view of the microwave radiometric sensor probe module of the present disclosure embodied as a speculum for receiving the housing of FIG. 1.

In an illustrative embodiment as shown in FIG. 2, a microwave radiometric sensor probe module 10 comprises a housing 30 having a microwave circuit housing portion 14 and an ear canal portion 40.

Figure 1:
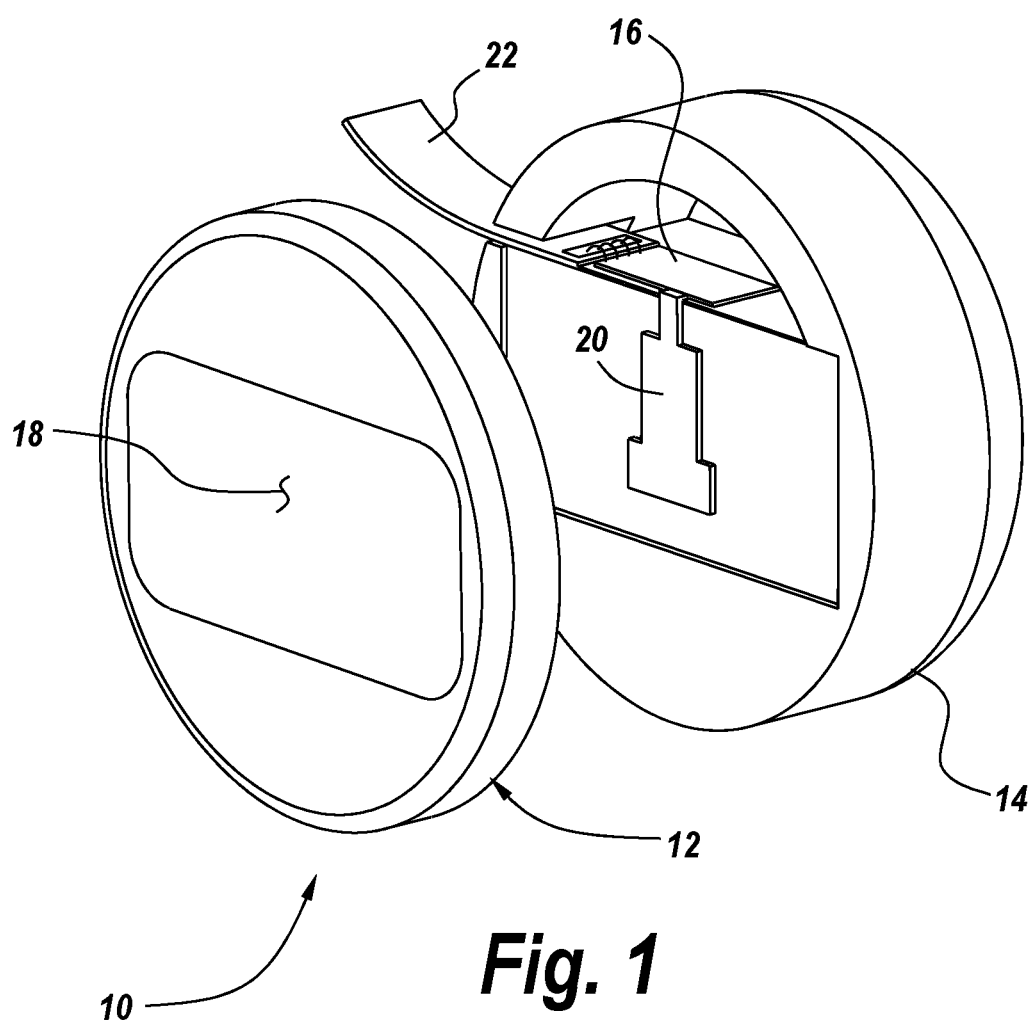
FIG. 1 is a perspective, partial section view of a microwave radiometric sensor probe module and housing according to the present disclosure.

The microwave circuit housing portion 14 is illustrated in greater detail in FIG. 1. It comprises a waveguide portion 12 shown temporarily separated from the remainder of the microwave circuit housing portion 14. Disposed within the microwave circuit housing portion is a microwave integrated circuit 16 mounted on a microstrip or TEM structure and associated data cable 22. In the illustrated embodiment, a ribbon cable is shown, though in alternative embodiments other cable structures may be employed. The cable is for providing bias voltage to the circuit and to convey electrical signals from the circuit to a temperature monitor and control unit 50, to be discussed subsequently. In a further embodiment, the microwave radiometric sensor probe module 10 comprises a transmitter communicatively coupled to the microwave integrated circuit for enabling the communication of the electrical signals to the temperature monitor and control unit, which itself is provided with a wireless receiver for this purpose.

The microwave integrated circuit 16 receives microwave energy detected by a passive microwave probe 20. The probe can be a rod or, when using a dielectric filled waveguide, a printed structure as shown in FIG. 1. The probe 20 is disposed within a rectangular waveguide 18, which is preferably filled with dielectric.

Figure 7:
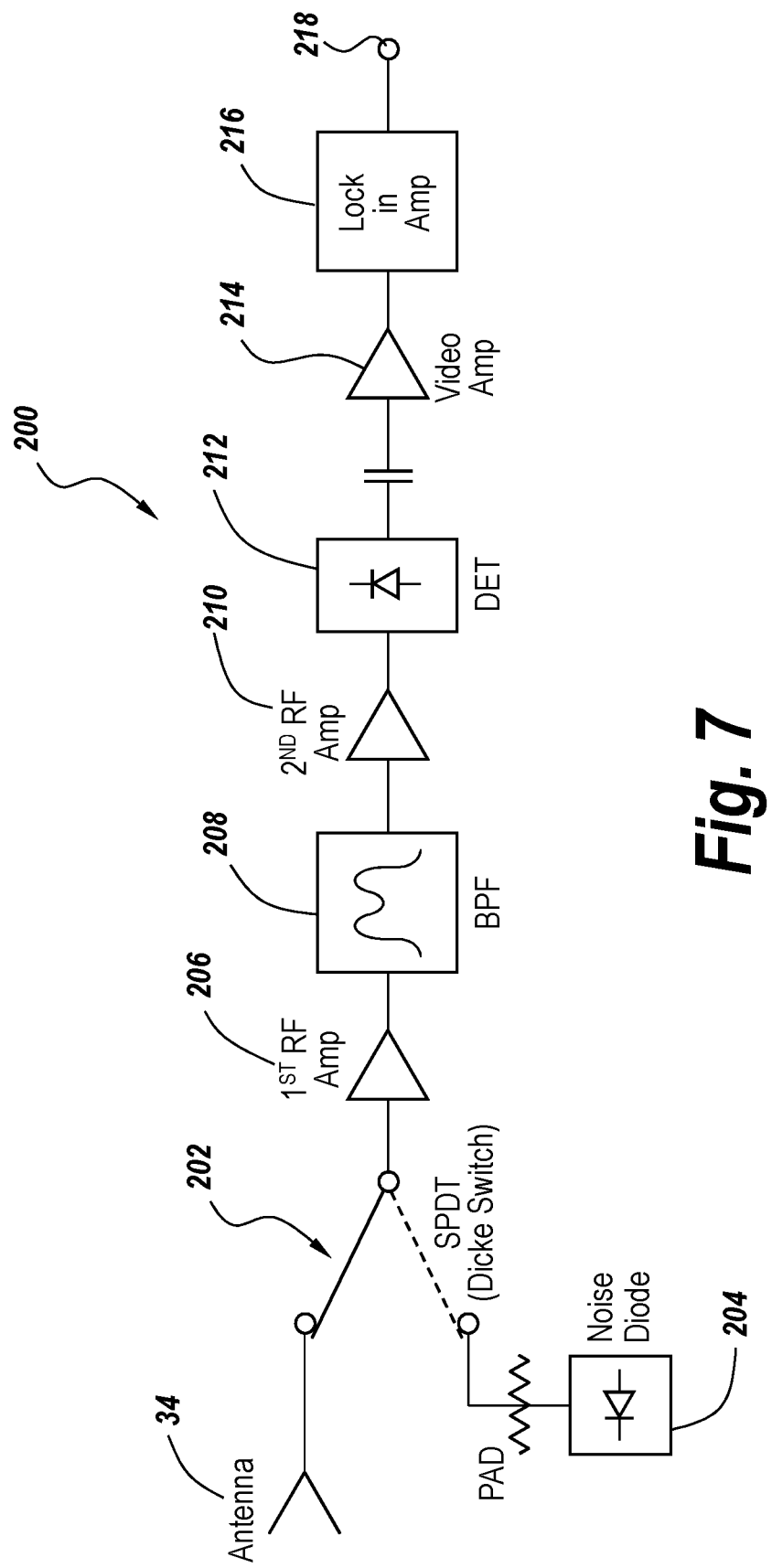
FIG. 7 is a schematic diagram of a radiometric sensor probe module 200 including a Dicke switch to be incorporated into the radiometric sensor module of FIG. 1.

With respect to FIG. 7, the microwave radiometric sensor probe module 10 employs a Dicke switch circuit 200 including a Dicke switch 202 with input from the antenna 34 (via the probe 20, not shown in FIG. 7 for simplicity). The input switch is switched at a constant rate between the immediate environment (the unknown or the target) as detected by the antenna and a fixed reference temperature at a noise diode 204. The switched or modulated microwave signal is therefore inserted at a point prior to microwave amplification and as close to the antenna 34 as possible. The input is then amplified and coherently detected. Specifically, the input passes through a first RF amplifier 206, a bandpass filter 208, a second RF amplifier 210, a square law detector 212, a video amplifier 214 and a lock-in amplifier 216 providing the radiometer output 218. The output 218 from the microwave integrated circuit is proportional to the temperature difference between the target temperature and the fixed and known reference temperature. Unwanted detector gain fluctuations below the frequency of the switching speed of the Dicke switch are suppressed. The output is provided to the temperature monitor and control unit 50 via the data cable 22.

As shown in FIG. 2, the microwave circuit housing portion 14 of the housing 30 interfaces to the ear canal portion 40 of the housing 30. The two portions may be provided of metal or metalized plastic to create the outer conductor of the microwave transmission line. The choice of material may be influenced by material and manufacturing cost and weight. For example, while aluminum could be used due to its light weight, plastic having an inner surface plated with gold or silver may provide improved microwave transmission. The two illustrated portions may be provided as discrete elements that are joined together such as through gluing or ultrasonic or heat welding. Alternatively, the portions of the housing may be formed as parts of a unitary structure.

The ear canal portion 40 has a tapered external surface that is contoured in much the same manner as an otoscope speculum for easy insertion into the ear canal of a patient, such as a newborn. In one embodiment, the speculum may also be provided with an outer layer of cushioning material for increased comfort, particularly when the sensor probe module is intended for long-term use.

The ear canal portion 40 comprises a cylindrical central bore forming a circular waveguide into which is disposed a dielectric rod antenna 34. The free end termination 36 pointed towards the passive microwave probe 20 forms the transition from a dielectric filled transmission line to an air filled rectangular waveguide 18. Radiation from the tympanic membrane is received at the dielectric rod antenna. A portion of the received energy is coupled into a surface wave within the dielectric rod antenna which travels along the antenna structure to the free end termination. The termination taper reduces the reflected surface wave to a negligible value. However, the overall length of the radiometric sensor probe module 10 can be reduced in alternative embodiments by replacing the taper with a quarter wave single step structure or by eliminating the taper altogether by going directly to the dielectric filled transmission line 18 and, in turn, to the probe 20.

The dielectric material selected for the antenna 34 and the dielectric filled waveguide 18 must be low loss, i.e. having a low loss tangent. The dielectric constant will for the most part be chosen by the size constraints of the structure. The size of the waveguide for a given frequency is reduced by the square root of the dielectric constant. Quartz, having a dielectric constant of four, would reduce the waveguide dimension by a factor of two. Quartz is also an excellent choice if the printed probe structure is to be plated.

Figure 3:
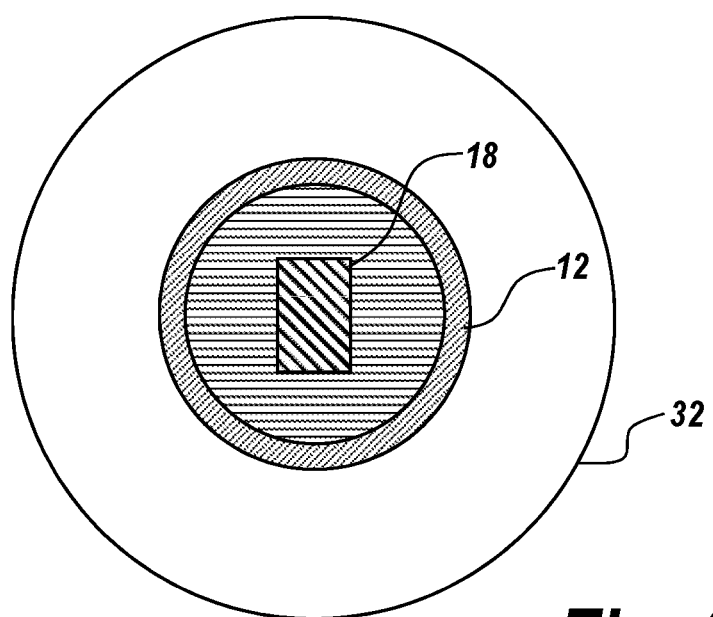
FIG. 3 is a cross-sectional view of the specula of FIG. 2 taken along lines 3-3.

The ear canal portion 40 also comprises a radial shield 32 extending orthogonally from the ear canal portion, such that an axis of symmetry of the radial shield is coaxial with an axis of symmetry of the housing 30. The radial shield may be seen in profile view in FIG. 2 and in cross-sectional view 3-3 in FIG. 3. It may be integral to the remainder of the housing 30 or may be affixed to the remainder of the housing 30 such as through gluing or welding. The radial shield is preferably provided of a lossy or absorptive plastic or, if not, then plated to be reflective to microwave radiation. It is also preferably dimensioned to inhibit the entry of external microwave radiation into the ear canal. It may be pliant such that when the housing 30 is inserted into the ear canal, the radial shield may abut the outer ear of the patient and may slightly deform in order to provide a tighter seal. The radial shield may also be peripherally disposed about the ear canal portion of the housing at a location that prevents a distal end of the housing, having the dielectric rod antenna, from being inserted too far into the ear canal, thereby avoiding contact damage to the tympanic membrane. While shown in FIG. 3 as circular, the radial shield may alternatively be shaped to loosely correspond to the typical shape of a human auricle for better fit. The radial shield may also serve to prevent over-insertion.

To ensure accuracy, the distance between the distal end of the probe module 10 and the tympanic membrane must be controlled to avoid the probe module making contact with the membrane. A reflection coefficient can be determined by the use of a noise injection radiometer. The injection of low level noise from the radiometer can be used to determine the match or percentage of the signal reflected. The reflection coefficient is best defined by the term Voltage Standing Wave Ratio (VSWR). It is the measurement of reflected power. For example, a VSWR of 2:1 would correspond to a reflected power of 10% and a VSWR of 3:1 would correspond to a reflected power of 25%. Ludeke and Kohler [ref 1] have suggested the use of a radiation-balancing radiometer employing noise injection to compensate for this reflection, thus making the received temperature equal to the object (the unknown) temperature to eliminate the error due to the reflectivity [ref 2].

[Ref 1] Ludeke K M, Kohler J: Microwave radiometric system for biomedical "true temperature" and emissivity measurements. J Microwave Power 18:277, 1983.

[Ref 2] Carr K L, Bielawa R J, Regan J F, et al: The effect of antenna match on microwave radiometric thermal patterns. IEEE MTT DIG F-5:189, 1983.

As an alternative to the use of the foregoing technique for measuring and controlling the distance between the distal end of the probe module 10 and the tympanic membrane, or in addition thereto, a soft interface 48 (FIG. 2) may be disposed upon the distal end to prevent contact of the antenna 34 or ear canal portion 40 with the tympanic membrane. This soft interface may be in the form of a soft foam pad or balloon filled with a powder or gel. This soft interface could then serve not only as a soft cushion but also as a matching structure between the rigid dielectric material of the antenna and the sensitive tissue of the tympanic membrane.

Figure 4:
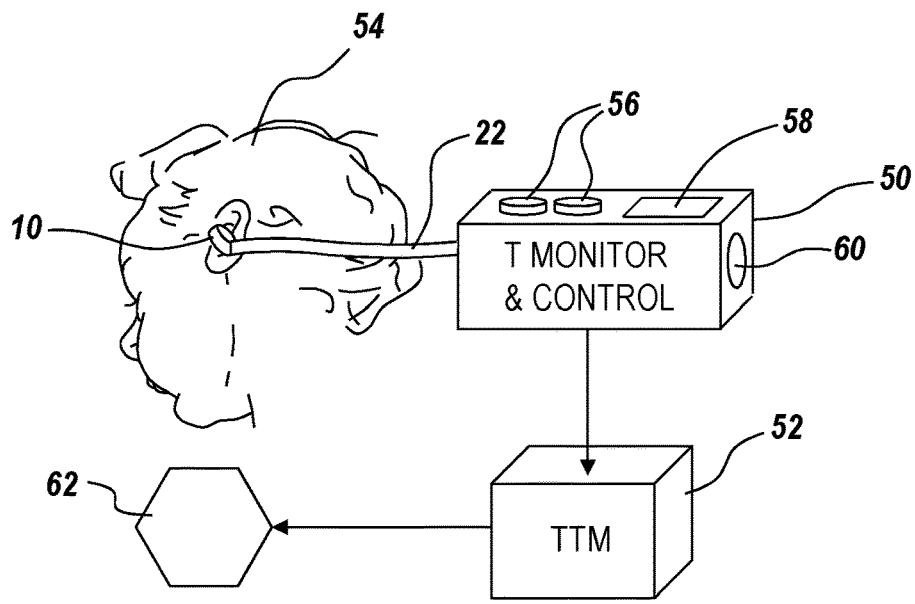
FIG. 4 is a block diagram illustrating the inter-relationship between the microwave radiometric sensor probe module of FIG. 2, a temperature monitoring and control unit, and a targeted temperature management (TTM) system.

The general arrangement of a system for monitoring and controlling the temperature of a patient using the microwave radiometric sensor probe module 10 is depicted in FIG. 4. The overall system may comprise, in addition to the microwave radiometric sensor probe module of FIGS. 1-3, a temperature monitor and control unit 50. In FIG. 4, the microwave radiometric sensor probe module has been disposed within the ear canal of a patient, in this case a newborn 54. A communications interface in the form of a data cable 22 electrically interconnects the module to the temperature monitor and control unit 50. In a further embodiment, the communications interface of the sensor probe module includes a low-power transmitter co-located with the microwave integrated circuit for communicating wirelessly with the temperature monitor and control unit. This latter unit receives a measure of the detected tympanic membrane radiation from the microwave integrated circuit in the sensor probe module via the low-power transmitter and derives a measure of brain temperature on the basis of a predefined correlation between detected tympanic radiation and brain temperature.

In addition, the temperature monitor and control unit 50 may be configured to derive a measure of respiration rate and/or heart rate from temporal fluctuations in the detected membrane radiation. This is achieved by recognizing the tympanic membrane is vascular, thin and tight. The heart beat appears as motion of the membrane and will modulate the noise emanated by the membrane and detected by the radiometer. The heart rate of a healthy, full term newborn is greater than 100 beats per minute. The respiratory rate is also detected as motion but at its much slower rate. Thus, the respiratory rate will be detected as a modulation of the heart rate.

The temperature monitor and control unit 50 is provided with one or more user interfaces 56 such as dials, pushbuttons, touchpads or the like for enabling a user to set a desired temperature value or a desired temperature profile over time. In further embodiments, the temperature monitor and control unit user interfaces enable a user to set a threshold respiratory rate value or range of values and a threshold heart rate value of range of values. The user interfaces may also be provided as a transceiver capable of receiving these user input values, profile, or ranges wirelessly such as via a cloud-based interface in communication with the transceiver. Such a cloud-based interface may be embodied in a mobile application or app running on a mobile device such as a mobile phone, tablet computer, or laptop computer.

The temperature monitor and control unit 50 also may also provide a user interface 58 such as an LCD or other display for displaying the derived brain temperature, the derived respiratory rate, and/or the derived heart rate to the user. In the alternative or in addition thereto, the user interface for displaying these derived values may be provided as a cloud-based transceiver having a display for visually presenting the derived values to a user. Further still, the temperature monitor and control unit may be provided with an annunciator 60 such as a speaker, buzzer, or light for alerting a user to a derived temperature that does not equal the desired temperature, either absolutely or within a predefined acceptable tolerance. The annunciator, which may be provided with an override or "silence" control, may also be for alerting a user to a derived respiratory rate or heart rate that exceeds or falls beyond a threshold value or range of values. However, in certain hospital environments, the use of such an annunciator would be disadvantageous or prohibited. Alternatively, the annunciator is a communications transceiver for issuing an alert message in the form of a control signal, text message, email or the like to a remote user such as at a nurse's station, the alert message conveying at least the respective derived values.

The disclosed system of FIG. 4 may further comprise a targeted temperature management (TTM) system 52. Such a system includes a patient temperature regulating article 62 such as a garment, blanket, head gear, or medical device that is arranged proximate to, about, on, or in the patient. For example, the temperature regulating article may be one or more of a cooling catheter, transnasal evaporative cooling cannulae, and a garment or skull cap having coolant flowing therethrough. The TTM system regulates the temperature of the temperature regulating article 62 on the basis of control input received from the temperature monitor and control unit 50. A closed loop feedback system is formed as the microwave radiometric sensor probe module 10 receives radiant energy from the tympanic membrane of the patient and conveys a measure of that radiant energy to the temperature control and monitor unit, the temperature control and monitor unit converts the conveyed measure of radiant energy into a measure of brain temperature, and the temperature control and monitor unit controls the TTM system according to the user-defined desired temperature value or desired temperature profile over time.

Figure 5:
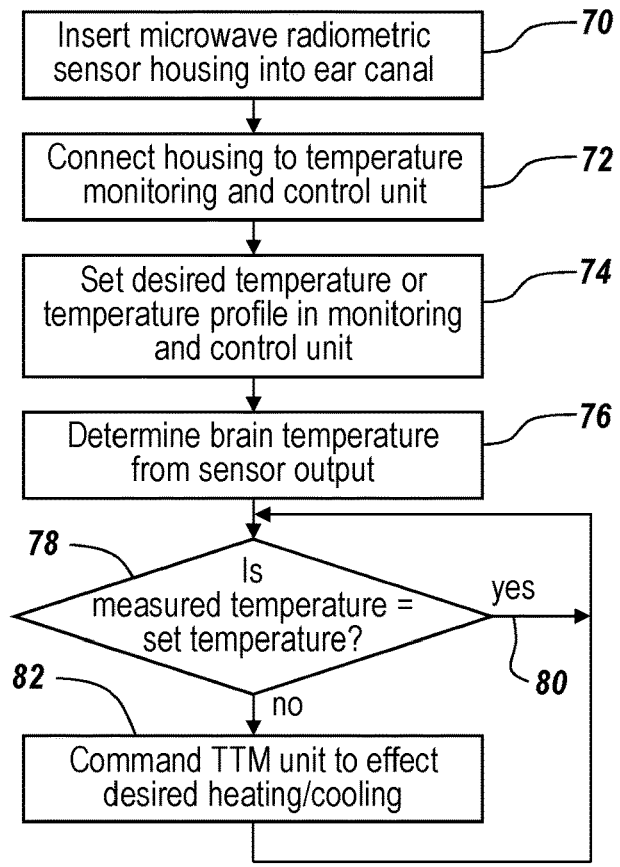
FIG. 5 is a flow diagram illustrating a method of monitoring the temperature of a patient using the microwave radiometric sensor probe module of FIG. 2 and selectively controlling the TTM system of FIG. 4.

A method of using the presently disclosed microwave radiometric sensor probe module 10 is described with respect to FIG. 5. The microwave radiometric sensor housing 30 is inserted 70 into the ear or auditory canal of a patient. The microwave integrated circuit 16 is connected 72 to the temperature monitor and control unit 52, either via a data cable 22 or wirelessly via a low-power transmitter disposed in the sensor housing 30 and in communication with the microwave integrated circuit 16. A user then sets 74 the desired temperature or temperature profile for the temperature monitor and control unit 50. This may be via a user interface 56 disposed on the temperature monitor and control unit itself or via a user interface provided on a wired or wirelessly interconnected remote transceiver such as a mobile device running a mobile app. The microwave radiometric sensor probe module 10 is then used to receive radiant energy from the tympanic membrane and to provide a sensor output to the temperature monitor and control unit, which derives 76 a measure of patient brain temperature from the sensor output. The temperature monitor and control unit assesses 78 whether the derived brain temperature value is equal to or is within a permitted tolerance range from the desired temperature or temperature profile. If so 80, the temperature monitor and control unit continues the monitoring function. Otherwise, the temperature monitor and control unit commands 82 the TTM unit to affect the necessary heating or cooling until the measured brain temperature value is equal to or is within a permitted tolerance range from the desired temperature or temperature profile.

Figure 6:
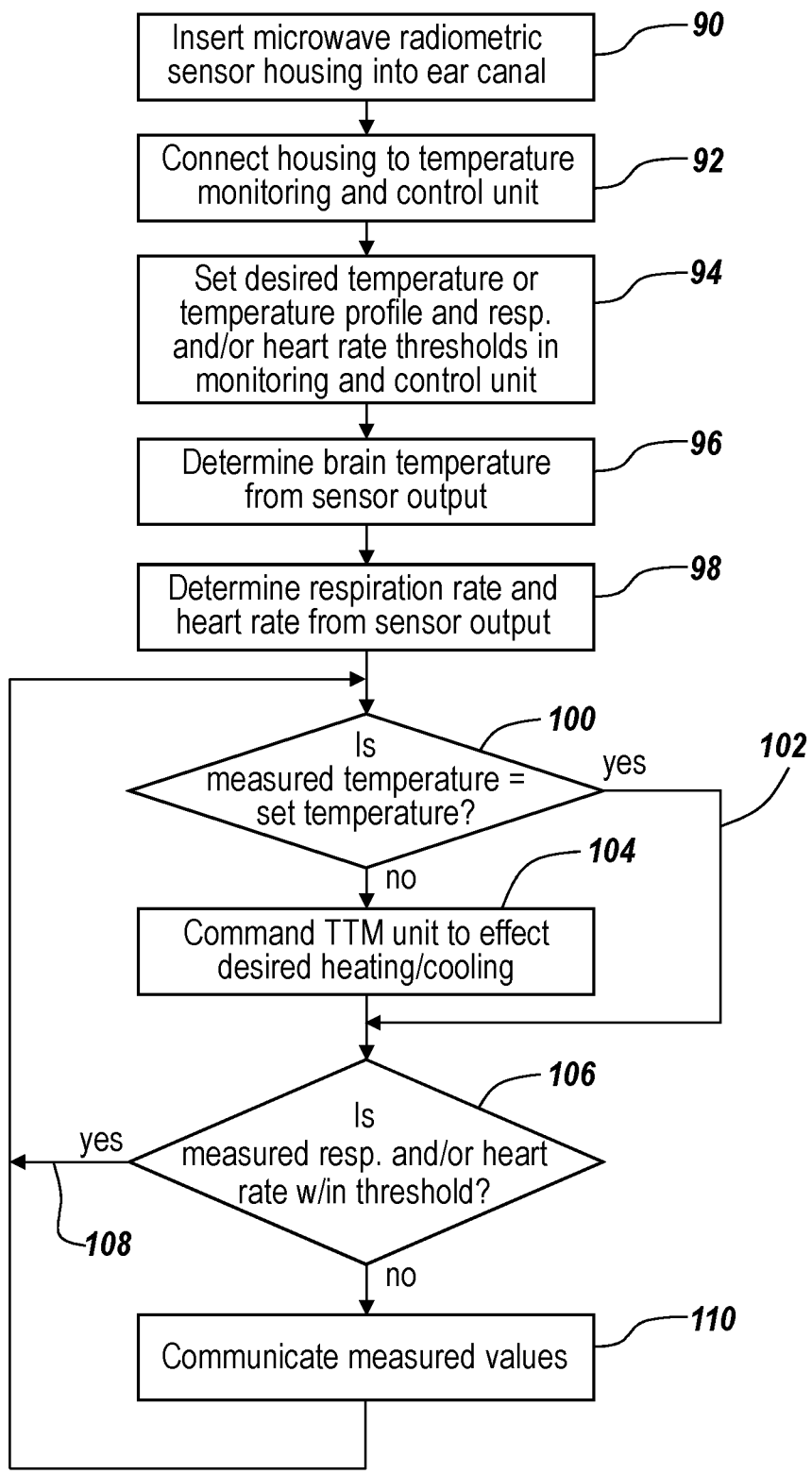
FIG. 6 is a flow diagram illustrating a method of monitoring the temperature, respiration rate, and heart rate of a patient using the microwave radiometric sensor probe module of FIG. 2 and selectively controlling the TTM system of FIG. 4.

A further method of using the presently disclosed microwave radiometric sensor probe module 10 is described with respect to FIG. 6. The microwave radiometric sensor housing 30 is inserted 90 into the ear or auditory canal of a patient. The housing is connected 92 to the temperature monitor and control unit 50, either via a physical data cable 22 or wirelessly via a low-power transmitter, as described above. A user then sets 94 the desired temperature or temperature profile and optionally the threshold respiratory rate and/or heart rate value(s) on the temperature monitor and control unit. The microwave radiometric sensor assembly is then used to receive radiant energy from the tympanic membrane and to provide a sensor output to the temperature monitor and control unit, which derives 96 a measure of patient brain temperature from the sensor output. Optionally, the temperature monitor and control unit also determines 98 a measure of respiration rate and/or heart rate from the sensor output. The temperature monitor and control unit then assesses 100 whether the measured brain temperature value is equal to or is within a permitted tolerance range from the desired temperature or temperature profile. If not, the temperature monitor and control unit commands 104 the TTM unit 52 to affect the necessary heating or cooling until the measured brain temperature value is equal to or is within a permitted tolerance range from the desired temperature or temperature profile, then the method optionally proceeds to the next step 106. Meanwhile, if the temperature monitor and control unit determines 102 that the measured brain temperature value is equal to or within a permitted tolerance range from the desired temperature or temperature profile, the method optionally proceeds to the next step 106. Here, the temperature monitor and control unit then assesses 106 whether the measured respiration rate and/or the heart rate is within (i.e. above or below) a respective threshold value or set of values. If so 108, the temperature monitor and control unit continues the monitoring function. If not, the temperature monitor and control unit communicates 110 the measured values to a user, such as via an alarm, which may be audible and/or visual such as through an annunciator 60 associated with the temperature monitor and control unit, or by displaying the measured values to a user at a remote device such as through the transmission of a text message, email, or other communication.

The procedures, processes, and/or modules described herein may be implemented in hardware, software, embodied as a computer-readable medium having program instructions, firmware, or a combination thereof. For example, the functions described herein may be performed by a processor executing program instructions out of a memory or other storage device.

The foregoing description has been directed to particular embodiments. However, other variations and modifications may be made to the described embodiments, with the attainment of some or all of their advantages. It will be further appreciated by those of ordinary skill in the art that modifications to the above-described systems and methods may be made without departing from the concepts disclosed herein. Accordingly, the invention should not be viewed as limited by the disclosed embodiments. Furthermore, various features of the described embodiments may be used without the corresponding use of other features. Thus, this description should be read as merely illustrative of various principles, and not in limitation of the invention.

Many changes in the details, materials, and arrangement of parts and steps, herein described and illustrated, can be made by those skilled in the art in light of teachings contained hereinabove. Accordingly, it will be understood that the following claims are not to be limited to the embodiments disclosed herein and can include practices other than those specifically described, and are to be interpreted as broadly as allowed under the law.

What is claimed is:

1. A microwave radiometric sensor probe assembly for detecting a temperature of a tympanic membrane of a patient, comprising:
    a housing having a microwave receiver circuit housing portion and an ear canal portion, the ear canal portion having an external surface configured to be received within an ear canal of the patient and the microwave receiver circuit housing portion configured to be disposed external to the ear canal of the patient when the ear canal portion is received within the ear canal of the patient;

a microwave integrated receiver circuit disposed within the microwave receiver circuit housing portion;

a waveguide formed within the microwave receiver circuit housing portion;

a passive microwave probe disposed within the waveguide and in electrical communication with the microwave integrated receiver circuit;

a dielectric waveguide antenna disposed within the ear canal portion for coupling radiation energy received from the tympanic membrane via the ear canal, and not via contact with the tympanic membrane, to the passive microwave probe; and dielectric material within the waveguide and intermediate the passive microwave probe and the dielectric waveguide antenna, wherein the passive microwave probe is configured to couple the radiation energy received from the tympanic membrane via the dielectric waveguide antenna to the microwave integrated receiver circuit.

2. The assembly of claim 1, further comprising a radial shield disposed on the external surface of the housing proximate an interface between the microwave receiver circuit housing portion and the ear canal portion.

3. The assembly of claim 2, wherein the radial shield is configured to block microwave signals from entering the ear canal when the ear canal portion of the housing is disposed within the ear canal of the patient.

4. The assembly of claim 2, wherein the radial shield is configured as a disc having an axis of symmetry coaxial to an axis of symmetry of the housing.

5. The assembly of claim 1, further comprising a data cable assembly in mechanical and electrical communication with the microwave integrated receiver circuit for providing electrical bias to the microwave integrated receiver circuit and for receiving one or more signals from the microwave integrated receiver circuit.

6. The assembly of claim 1, further comprising a soft interface disposed at a distal end of the dielectric waveguide antenna, towards the tympanic membrane when disposed within the ear canal of the patient.

7. The assembly of claim 6, wherein the soft interface is a foam pad or balloon.

8. A system for monitoring and controlling a temperature of a patient, comprising:

a microwave radiometric sensor probe assembly, comprising a housing having a microwave receiver circuit housing portion and an ear canal portion, the ear canal portion having an external surface configured to be received within an ear canal of the patient and the microwave receiver circuit housing portion configured to be disposed external to the ear canal of the patient when the ear canal portion is received within the ear canal of the patient, a microwave integrated receiver circuit disposed within the microwave receiver circuit housing portion, a waveguide formed within the microwave receiver circuit housing portion, a passive microwave probe disposed within the waveguide and in electrical communication with the microwave integrated receiver circuit, a dielectric waveguide antenna disposed within the ear canal portion for coupling radiation energy received from a tympanic membrane via the ear canal, and not via contact with the tympanic membrane, to the passive microwave probe, dielectric material within the waveguide and intermediate the passive microwave probe and the dielectric waveguide antenna, the passive microwave probe configured to couple the radiation energy received from the tympanic membrane via the dielectric waveguide antenna to the microwave integrated receiver circuit, and a communications interface associated with the microwave integrated receiver circuit for conveying one or more signals from the microwave integrated receiver circuit; and a temperature monitor and control unit, external to the ear canal of the patient when the ear canal portion is received within the ear canal of the patient, in electrical communication with the microwave radiometric sensor probe assembly via the communications interface, for receiving the conveyed one or more signals from the microwave integrated receiver circuit and for determining a measure of the tympanic membrane temperature of the patient therefrom.

9. The system of claim 8, wherein the temperature monitor and control unit comprises a user interface for providing a representation of the determined measure of tympanic membrane temperature to a user.

10. The system of claim 8, wherein the temperature monitor and control unit comprises a user interface for enabling a user to define a desired temperature or temperature range for the measure of tympanic membrane temperature of the patient.

11. The system of claim 10, wherein the user interface is further for enabling the user to define a desired temperature profile or temperature range profile over a period of time.

12. The system of claim 8, wherein the temperature monitor and control unit is further for correlating the determined measure of tympanic membrane temperature to an estimate of a brain temperature of the patient.

13. The system of claim 8, further comprising a targeted temperature management system for adjusting the temperature of the patient, the targeted temperature management system being communicatively coupled to the temperature monitor and control unit and being operative to adjust the temperature of the patient in response to input from the temperature monitor and control unit.

14. The system of claim 13, wherein the targeted temperature management system comprises a patient temperature control article selected from the group consisting of a cooling catheter, transnasal evaporative cooling cannulae, and a patient-worn garment or skull cap having coolant flowing therethrough.

15. The system of claim 8, wherein the microwave radiometric sensor probe assembly further comprises a radial shield disposed on the external surface of the housing proximate an interface between the microwave receiver circuit housing portion and the ear canal portion, the radial shield for blocking the entry of external microwave signals from entering the ear canal when the ear canal portion of the housing is disposed within the ear canal of the patient.

16. The system of claim 8, wherein the communications interface is a data cable.

17. The system of claim 8, further comprising a soft interface disposed at a distal end of the dielectric waveguide antenna, towards the tympanic membrane when disposed within the ear canal of the patient.

18. The system of claim 17, wherein the soft interface is a foam pad or balloon.

19. A method of deriving a measure of brain temperature of a patient, comprising:
   detecting radiation naturally emitted by a tympanic membrane of the patient with a microwave radiometric sensor probe module disposed at least partially within an ear canal of the patient;
   conveying signals representative of the detected radiation emitted by the tympanic membrane to a temperature monitor and control unit; and
   deriving the measure of brain temperature of the patient from the conveyed signals representative of the detected radiation naturally emitted by the tympanic membrane,
   wherein the microwave radiometric sensor probe module comprises
   a housing having a microwave receiver circuit housing portion and an ear canal portion, the ear canal portion having an external surface configured to be received within an ear canal of the patient and the microwave receiver circuit housing portion configured to be disposed external to the ear canal of the patient when the ear canal portion is received within the ear canal of the patient;
   a microwave integrated receiver circuit disposed within the microwave receiver circuit housing portion;
   a waveguide formed within the microwave receiver circuit housing portion;
   a passive microwave probe disposed within the waveguide and in electrical communication with the microwave integrated receiver circuit;
   a dielectric waveguide antenna disposed within the ear canal portion for coupling radiation energy received from the tympanic membrane via the ear canal, and not via contact with the tympanic membrane, to the passive microwave probe; and
   dielectric material within the waveguide and intermediate the passive microwave probe and the di electric waveguide antenna,
   wherein the passive microwave probe is configured to couple the radiation energy received from the tympanic membrane via the dielectric waveguide antenna to the microwave integrated receiver circuit.

20. The method of claim 19, further comprising:
   comparing the derived measure of brain temperature of the patient with a desired temperature value or range of values.

21. The method of claim 20, further comprising:
   controlling a targeted temperature management system in response to the comparison of the derived measure of brain temperature of the patient with the desired temperature value or range of values, the targeted temperature management system for selectively cooling a body of the patient.

22. The method of claim 19, further comprising deriving at least one of a measure of respiratory rate and a measure of heart rate of the patient from the conveyed signals representative of the detected radiation emitted by the tympanic membrane.

23. The method of claim 22, further comprising displaying the derived at least one of the measure of respiratory rate and the measure of heart rate to a user.

24. A method of controlling a brain temperature of a patient, comprising:
   disposing a microwave radiometric sensor probe assembly within an ear canal of the patient, the assembly comprising
   a housing having first and second portions,
   a microwave integrated receiver circuit disposed within the housing first portion,
   a waveguide formed within the housing first portion,
   a passive microwave probe disposed within the housing first portion and in electrical communication with the microwave integrated receiver circuit,
   a dielectric waveguide antenna disposed within the housing second portion,
   dielectric material within the waveguide and intermediate the passive microwave probe and the dielectric waveguide antenna, the passive microwave probe being configured to couple radioactive energy received from a tympanic membrane by the dielectric waveguide antenna via the ear canal and not via contact between the tympanic membrane and the dielectric waveguide antenna to the microwave integrated receiver circuit, and
   a communications interface associated with the microwave integrated receiver circuit for providing externally applied electrical bias to the microwave integrated receiver circuit and for conveying signals from the microwave integrated receiver circuit;
   electrically connecting the microwave radiometric sensor probe assembly to a temperature monitor and control unit;
   electrically connecting the temperature monitor and control unit to a targeted temperature management system for controlling the brain temperature of the patient;
   setting a target brain temperature or temperature range in association with the temperature monitor and control unit;
   deriving a measure of the brain temperature of the patient, by the temperature monitor and control unit, from a measure of the tympanic membrane temperature of the patient from the radiative energy emitted by the tympanic membrane of the patient, collected by the dielectric waveguide antenna, communicated to the passive microwave probe, received by the microwave integrated receiver circuit, and conveyed to the temperature monitor and control unit via the communications interface; and
   controlling the targeted temperature management system, by the temperature monitor and control unit, in response to the target brain temperature or temperature range and the derived measure of brain temperature,
   wherein the housing second portion has an external surface configured to be received within an ear canal of the patient and the housing first portion configured to be disposed external to the ear canal of the patient when the housing second portion is received within the ear canal of the patient.

* * * * *